United States Patent [19]

Shaposka et al.

[11] Patent Number: 4,793,880
[45] Date of Patent: Dec. 27, 1988

[54] STERILE WELDING OF PLASTIC TUBES

[75] Inventors: John B. Shaposka; Dudley W. C. Spencer, both of Wilmington, Del.

[73] Assignee: Denco, Inc., Wilmington, Del.

[21] Appl. No.: 51,390

[22] Filed: May 18, 1987

[51] Int. Cl.⁴ .......................... A61M 5/00; B29C 65/20
[52] U.S. Cl. ...................................... 156/158; 156/159; 156/304.2; 156/304.6; 156/499; 156/503; 604/905
[58] Field of Search ................... 156/158, 304.2, 304.6, 156/499, 502, 503, 159, 258, 304.5; 604/905, 29; 285/260, 155, 156

[56] References Cited

U.S. PATENT DOCUMENTS 3,035,631  5/1962  Knowles ............................. 156/579
4,505,780  3/1985  Sewards ........................... 156/304.6
4,610,670  9/1986  Spencer ................................ 604/905
4,619,642  10/1986 Spencer .................................. 604/29
4,737,214  4/1988  Leurink et al. ...................... 156/158

Primary Examiner—Michael Wityshyn
Attorney, Agent, or Firm—Connolly & Hutz

[57] ABSTRACT

A linear welding process and apparatus connects fluid-filled tubes in a sterile manner. The linear welder includes a base on which a carriage is slidably mounted. A pair of side by side arms are secured to the carriage as are a pair of tube holders. A pair of clamping jaws are mounted on the arms to clamp a pair of tubes in the holders. The arms are movable for passing the clamped tubes into contact with a heated wafer which cuts the tubes into tube sections. The tube sections are realigned and a pair of sections are butt welded together.

31 Claims, 8 Drawing Sheets

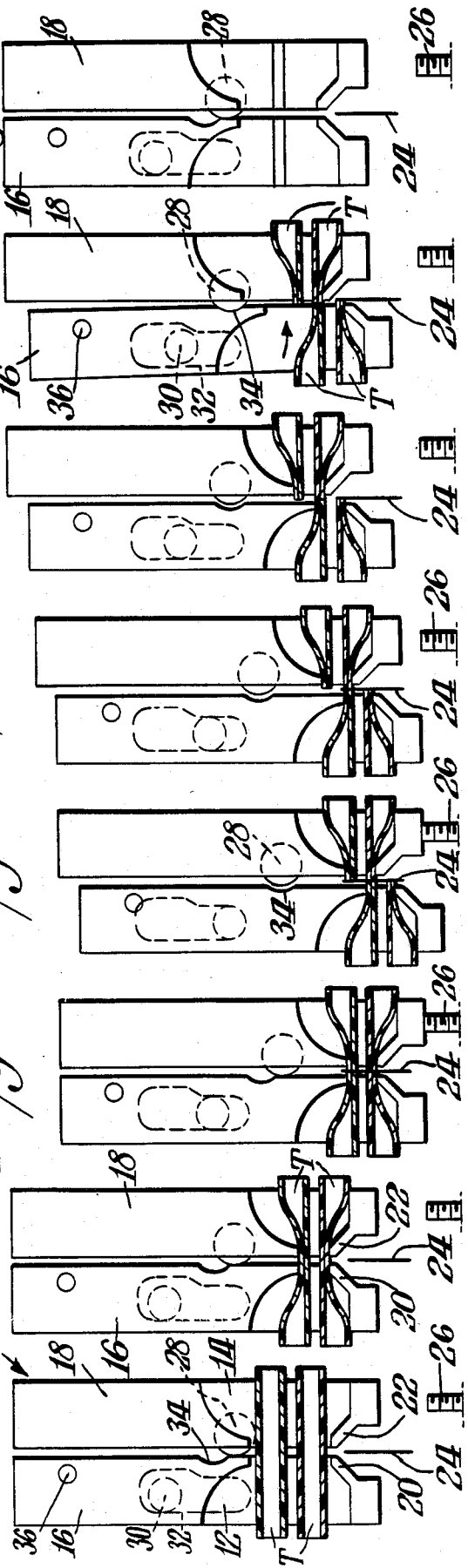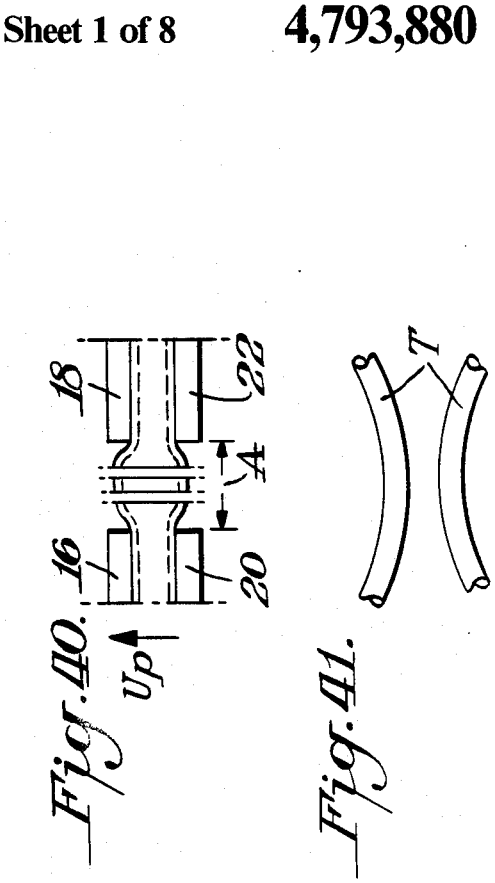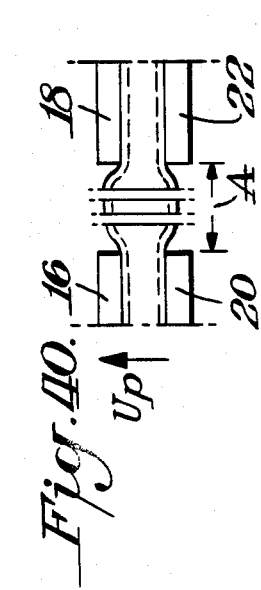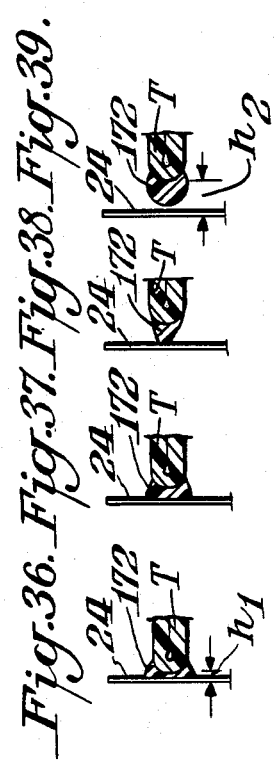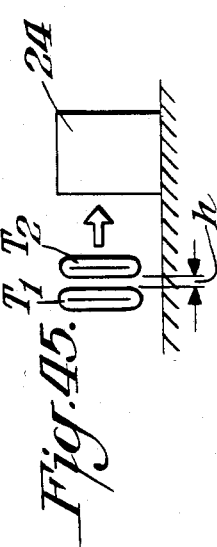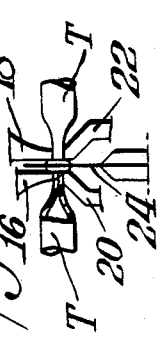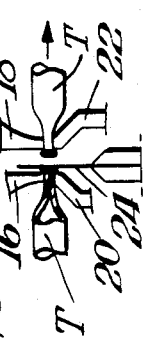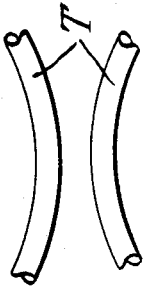

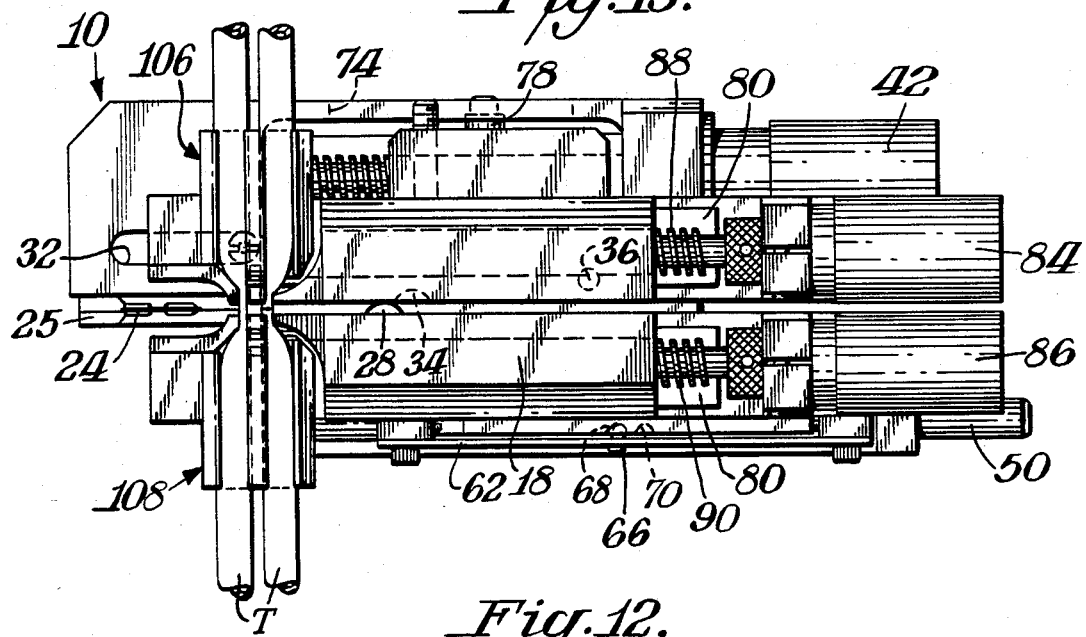
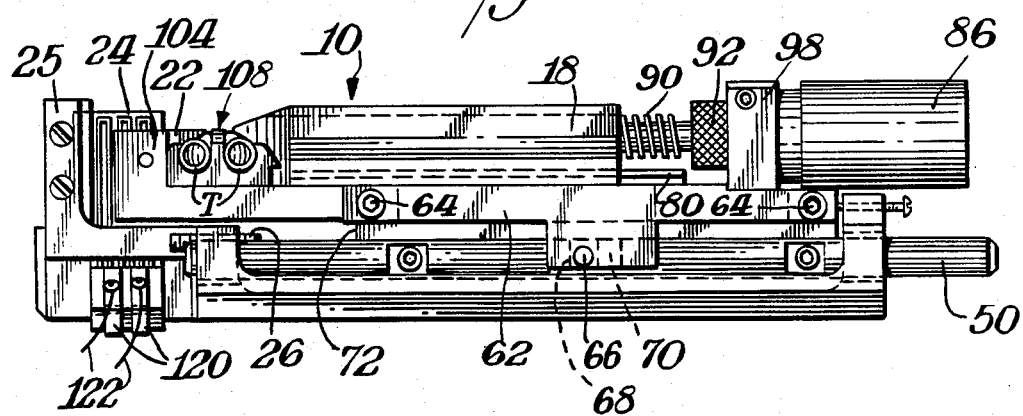
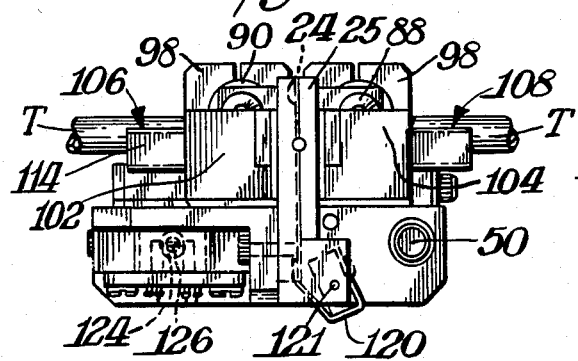
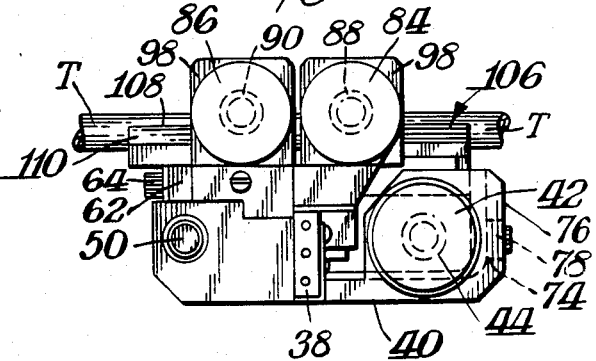

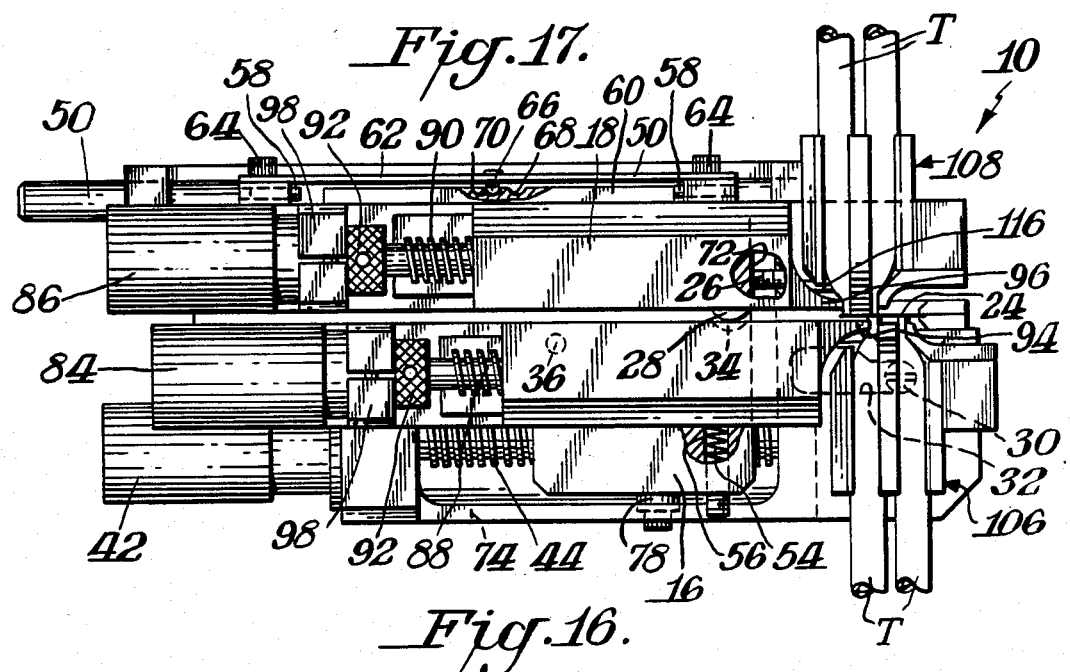
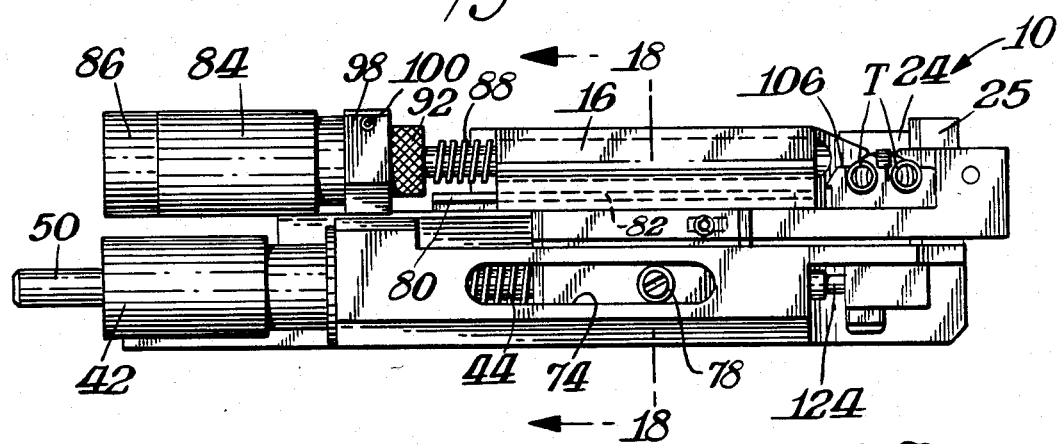
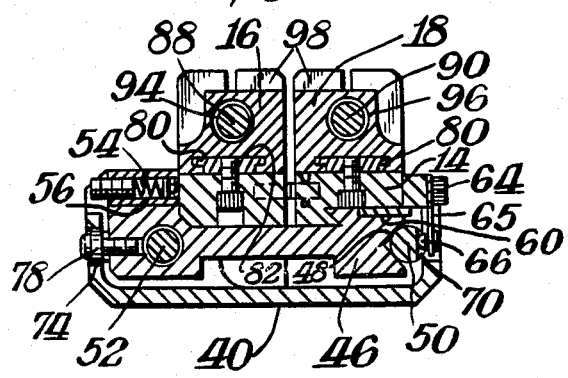
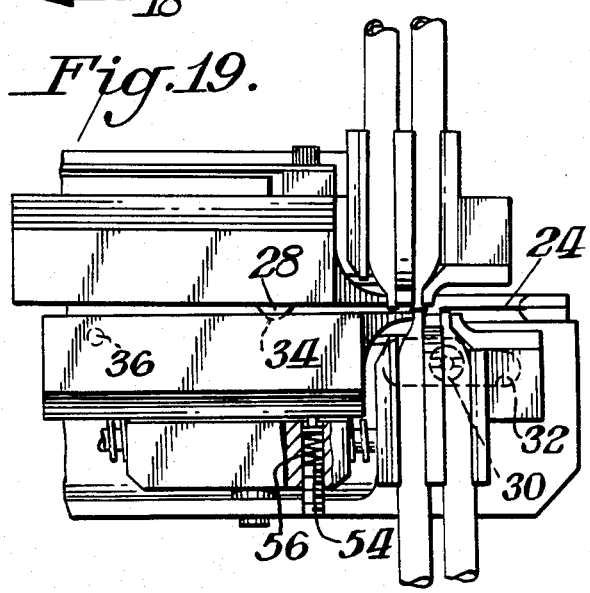

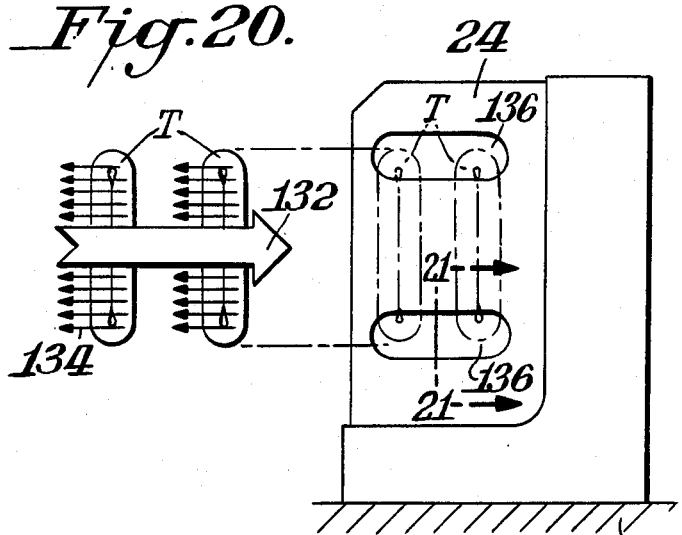
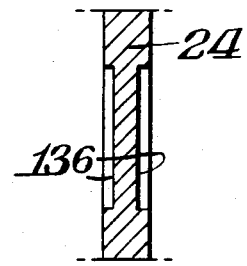
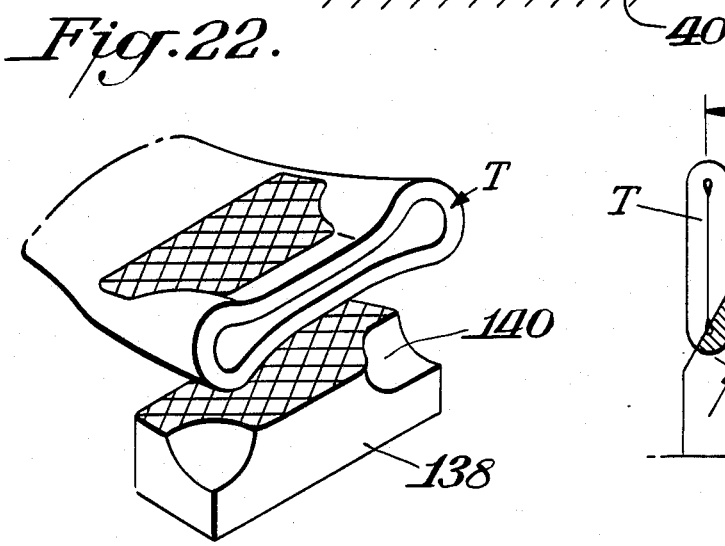
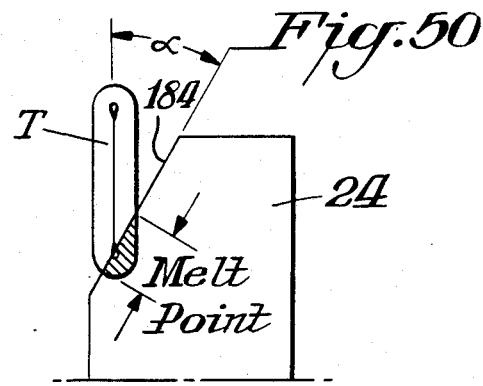
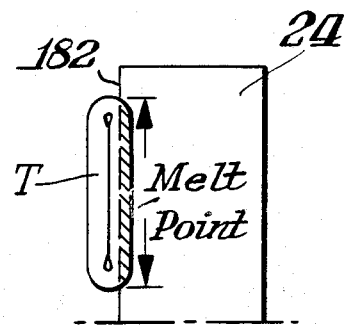

STERILE WELDING OF PLASTIC TUBES

BACKGROUND OF THE INVENTION

The basic weld cycle necessary for sterily welding round, dry tubing is known in the art and is currently being practiced in the form of the DuPont SCD-I (U.S. Pat. No. 4,369,779). In attempting to extend the technology to fluid-filled tubes that welder was modified primarily by the incorporation of a set of tube clamps which flatten the tube in the area immediately adjacent to either side of the future weld site, and also by various minor changes to the weld cycle. The clamping operation excludes most of the fluid from the weld zone and makes it possible to join the tubes mechanically (but not necessarily sterily). This device is known as the DuPont SCD-II (U.S. Pat. No. 4,610,670).

The problem with the SCD-II is the flattening operation was "grafted on" to the existing SCD-I with only minor changes to the weld cycle. For some sizes of tubing SCD-II will produce sterile welds, but for other sizes the weld integrity will suffer.

The cause is in the flattening of the tubing prior to welding. During this process large stresses are built-up in the folding area of the tube. These stresses make it difficult to produce a reliable, sterile seal in that area. In addition, the motion of the tubes and their orientation during the re-alignment operation can cause viable spores to be drawn into the lumen area of the weld site.

SUMMARY OF INVENTION

An object of this invention is to provide a welder and process which overcomes the deficiencies of the prior art.

A further object of this invention is to provide such a welder and process in which the tubes are flattened without the opposed walls actually touching.

A still further object is to provide such a welder and process wherein the cutting takes place at a non-flat point of the tubing and wherein the tubing is self-opening after being joined.

The present invention is the result of "going back to basics" in the examination of the process of welding fluid-filled tubes. The entire welding process has been redefined in order to compensate for the weaknesses induced by the tube flattening operation.

Specifically, the invention involves:

Defining a new weld motion so that welding occurs in a linear fashion—i.e. the tubes follow a straight path onto the wafer and retrace that path in coming off of the wafer.

Inserting a "heat soak pause" wherein the tubes to be welded are moved (after severing and re-aligning) to a point as close to the edge of the wafer as possible. The tubes are allowed to dwell at this position to insure that a large, hot PVC melt pool is available for the welding operation and that the pool is depleted as little as possible while moving from the heat soak point to the weld point.

Adding an adjustable fixed-stop to the shift motion so that the misalignment in the weld is eliminated.

These changes result in:

melted PVC on the wafer is not wasted because the tubes pass back over it during the retrace step.

allows the wafer to be "contoured" so that less PVC is removed from the fold areas allowing them to be significantly stronger.

minimizes the depletion of the PVC melt pool during the last (critical) part of the cycle since the molten tube ends have to travel the absolute minimum distance from the heat soak point to the weld point.

allows contouring of heat pattern on the wafer.

allows the optional formation of a connecting web between the stubs and the welded tubes as an aid to re-establishing the lumen.

In accordance with this invention the welding process consists of mounting the tubes to be welded in suitably contoured movable holders. The tubes are next flattened towards a plane that is perpendicular to the direction of welding motion. The hot cutting means is brought up to temperature and welding commences: first, both tubes are severed by the cutting means. The direction of motion and the arrangement of the tubes is such that the tubes are severed one after the other (instead of simultaneously as in the DuPont SCD). Further, the second tube follows the same path as the first. Also, since the flattened section of the tubes is perpendicular to the line of motion of the tubes, the hot cutting means can be contoured to allow the severed ends of the tubes to assume any desired shape prior to the welding. As soon as both tubes have been severed, one clamp arm (the shift arm) hits an adjustable stop while the other arm (the pivot arm) continues on until the tubes to be welded are aligned. At this point, the motion of the clamp arms reverses and the both begin to retrace their path (locked in the shifted position) back through the PVC deposited on the wafer during the cut stroke. The motion continues until the tubes to be welded are just at the edge of the cutting means where the motion stops to allow the tube ends to thoroughly melt and all bacteria and spores to be killed. The motion then begins again and the tubes are pulled off the cutting means and the two molten tube ends urged together to make the weld. The tubes can now be removed and the lumen reestablished by simply pulling the stub ends away from the welded tube.

In accordance with this invention the welder effects a contoured flattening of the tubing sections so that the inside walls are almost but still out of contact with each other. The tube sections are cut by a hot wafer which may be contoured. The fluid contents in the tubes are vaporized adjacent the hot wafer with a vapor barrier being formed. The cut tube sections are realigned and two sections are butt welded together. After the joint has cooled it resumes its normal lumen shape when released from the welder clamps without further stress on the tubes.

The welder, which may be considered a linear welder, includes a stationary base on which is slidably mounted a carriage for moving a pair of arms mounted on the carriage. Each arm carries a clamping jaw which is driven into contact with a tube in the tube holder. One of the arms is a shift arm which is limited in its movement so that the other arm (the pivot arm) can be moved forwardly thereof to effect the realignment of the cut tube sections. The pivot arm is then moved toward the shift arm to effect the butt welding.

THE DRAWINGS

FIGS. 1–8 are plan views schematically showing the different steps in the operation of the linear welder in accordance with this invention;

FIG. 12 is a side elevation view of the linear welder of this invention in the phase of operation shown in FIG. 2;

FIG. 13 is a top plan view of the linear welder shown in FIG. 12;

FIGS. 14-15 are front and rear elevation views of the linear welder shown in FIGS. 12-13;

FIG. 16 is a side elevation view of the linear welder of this invention in the phase of operation shown in FIG. 4;

FIG. 17 is a top plan view of the linear welder shown in FIG. 16;

FIG. 18 is a cross-sectional view taken through FIG. 16 along the line 18—18;

FIG. 19 is a top plan view of the linear welder of this invention in the phase of operation shown in FIG. 7;

FIG. 20 is a side elevation view of a portion of the linear welder of this invention in accordance with a different aspect of this invention;

FIG. 21 is a cross-sectional view taken through FIG. 20 along the line 21—21;

FIG. 22 is a perspective view showing a novel clamping jaw which may be used in the linear welder of this invention;

FIGS. 34-35 are top plan views with FIG. 34 being partly in section showing stub sealings steps in accordance with this invention;

FIGS. 36-39 are enlarged cross-sectional elevational views showing the sequence of steps in accordance with the stub sealing aspect of FIGS. 34-35;

FIG. 40 is a front elevation view showing the tubes in their flattened condition;

FIGS. 41-42 are plan views of tube supports in accordance with this invention;

FIG. 45 is a side elevation view illustrating a pair of tubes about to be cut by a wafer;

FIG. 49 is a side elevation view showing a wafer tube arrangement; and

FIG. 50 is a view similar to FIG. 49 showing a modified wafer.

DETAILED DESCRIPTION

Figure 10:
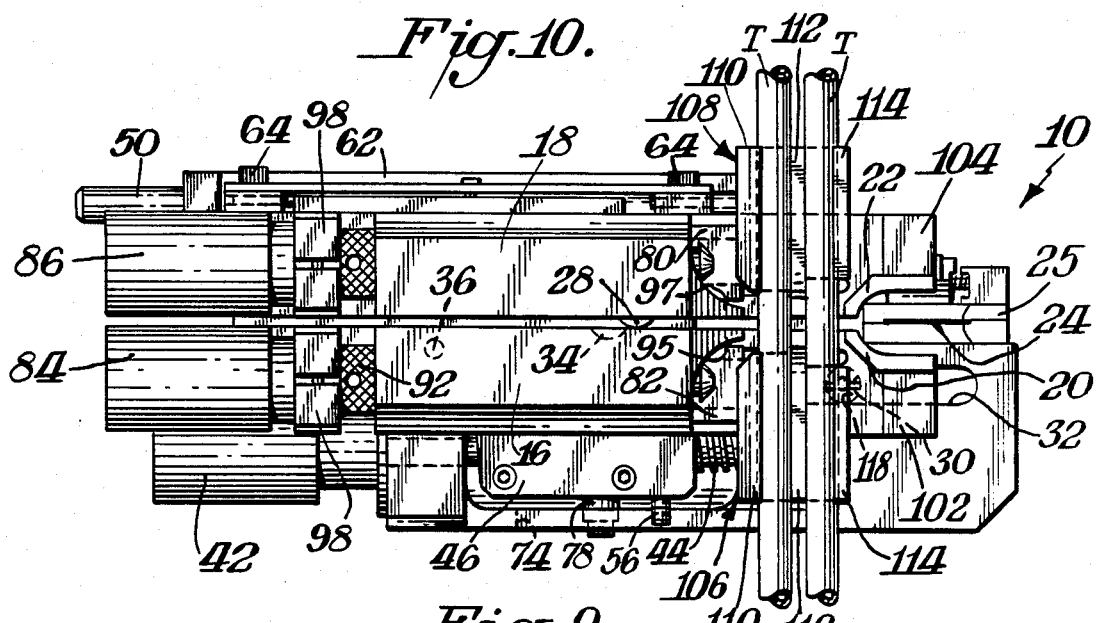
FIG. 10 is a top plan view of the linear welder shown in FIG. 9.

FIGS. 1-8 illustrate the general operation of the linear welder 10 in accordance with this invention. The details of linear welder 10 are better shown in FIGS. 9-19. FIGS. 1-8, however, show sufficient details to understand the general operation. As indicated in FIGS. 1-8 a pair of tubes are inserted in a pair of tube holders across arms 12, 14. A clamping jaw 16, 18 is mounted on each respective arm 12, 14. Fixed clamping jaws 20, 22 are mounted on the respective arms 12, 14 on the opposite sides of tubes T, T. FIG. 1 illustrates linear welder 10 in the initial step of operation, wherein the tubes have been loaded or mounted in welder 10.

FIG. 2 illustrates the next phrase of operation, wherein the tubes are flattened and the cutting wafer 24 is heated. In this phase of operation, clamping jaws 16, 18 are moved forwardly into contact with one of the tubes T. The tube holders are slidably mounted on arms 12, 14 so that the forward movement of clamping jaws 16, 18 against its tube results in driving the tube holders forwardly with the other tube thereby being pressed into contact with fixed clamping jaws 20, 22 resulting in the tubes T, T being moved to a flattened condition. The portion of the tubes in the spacing between the sets of clamping jaws might still be partially opened and might contain fluid therein.

FIG. 3 illustrates the next stage of operation, wherein the two tubes T, T are cut into four tube sections. This is accomplished by moving both arms 12, 14 forwardly so that the heated wafer 24 which lies in the spacing between the arms and tube holders and is in the path of movement of the tubes and cuts through the clamped tubes in a manner known in the art. As shown in FIG. 3 a stop member 26 is provided to limit the forward movement of arm 14.

FIG. 4 shows the stage of operation wherein the tubes are realigned so that two of the tube sections become aligned with each other. This realignment is accomplished by moving arm 12 forwardly until its upstream tube section is in line with the downstream tube section of arm 14. Since arm 14 is displaced from arm 12, arm 14 is designated as a shift arm. As illustrated in FIGS. 1-3 during the initial stages of operation the spacing between arms 12 and 14 is maintained by, for example, a roller 28 mounted to arm shift 14 and riding on the surface of arm 12. Additionally, arm 12 includes a roller or cam follower 30 which rides against the surface of a cam track 32 located in the base of welder 10 which is later referred to in detail with respect to FIGS. 9-19.

FIG. 5 illustrates the condition of linear welder 10 during the heat soak step and before the welding step. As shown in FIG. 5, roller 28 is now located in detent or depression 34 on the surface of arm 12. The spacing between arms 12 and 14, however, is maintained because cam follower 30 is in the narrow portion of the slotted cam track 32. In the phase of operation illustrated in FIG. 5, arms 12 and 14 are jointly moved in the rearward direction so as to come out of contact with wafer 24.

FIG. 6 illustrates the next phase of operation wherein the realigned tube sections are butt welded together. As shown therein arms 12, 14 have moved rearwardly a sufficient distance so that cam follower 30 is in the widened portion of cam track 32. Roller 28 remains in detent or recess 34. Arm 12 is pivotally mounted at pivot point 36 and is urged in any suitable manner as later described to rotate toward shift arm 14. This rotational movement forces the heated cut ends of the realigned tube sections into contact with each other and thereby effect the butt welding. Since arm 12 is pivotally mounted, arm 12 is designated as a pivot arm.

FIG. 7 shows the next phase of operation wherein the tubes are unclamped and removed from welder 10.

FIG. 8 shows welder 10 in its reset condition. As schematically shown therein, pivot arm 18 contacts a micro-switch 38 which conditions the motor drives used in welder 10 for reversing their direction of movement.

FIGS. 9-19 illustrate in greater detail the various components of welder 10. Welder 10 comprises a chassis or fixed base 40 upon which is stationarily mounted the wafer 24 in any suitable manner such as by upstanding bracket 25. Base 40 also has secured thereto a motor 42 with a lead screw 44 (FIGS. 9-10) for driving a carriage 46 which rests on base 40. As best shown in FIG. 18, carriage 46 has a V-groove 48 along one side thereof in which is mounted a guide rod 50 which slides in bearings mounted to base 40. Carriage 46 also includes an internally threaded bore 52 which is engaged by lead screw 44 to control the forward and rearward movement of carriage 46. The guide rod 50 acts in conjunction with a roller 78 riding in slot 74 of upstanding wall 76 of base 40 to assure proper alignment of carriage 46 as it slides over base 40.

Arms 12, 14 are mounted on carriage 46. Arm 12 is mounted in a fixed position by means of pivot rod 36. Arm 14, however, is mounted in such a manner that it may move with respect to carriage 46. As shown in FIGS. 17-18, a bar 60 on carriage 46 is mounted for contacting screws 58 to limit the extent of motion of carriage 46. Screws 58 are adjustable to comprise adjustable stops and thereby control the extent of movement of carriage 46. Proper axial alignment between shift arm 14 and carriage 46 is assured by an elongated leaf spring member 62 secured to arm 14 at opposite ends of spring member 62 in any suitable manner such as by fasteners 64 (See FIG. 17). Spring member 62 has a depending flange 65 which carries a projection 66. Guide rod 50 in turn has a pair of notches or detents 68, 70. During the initial stages of operation projection 66 is located in notch 68 to lock arm 14 to carriage 46. When welder 10, however, is in the phase of operation illustrated in FIG. 3, arm 14 is prevented from further forward movement although carriage 46 continues to move forwardly. This stop means includes a projection or stop member 26 mounted to base 40 in the path of movement of edge 72 on arm 14. As carriage 46 continues to move forwardly projection 66 is popped out of detent 68 by means of its spring mounting and snaps into detent 70, so that arm 14 is again locked to carriage 46 and will travel with carriage 46 in the reverse direction.

Each arm 12, 14 includes a T-track or rail 80 (FIG. 18) for fitting in a corresponding by shaped groove 82 in the slidable clamping jaws 16, 18, thus providing a track for guiding the clamping jaws. A motor 84, 86 is provided for each sliding clamping jaw 16, 18, respectively with a lead screw 88, 90 being secured to a respective motor. Each lead screw includes a knurled collar 92 to permit manual adjustment of the lead screws. Each clamping jaw 16, 18, includes an internally threaded bore 94, 96, respectively, for engagement with a corresponding lead screw. Accordingly, the direction of rotation of the lead screws 88, 90 control the direction of movement of clamping jaws 16, 18. Clamping jaws 16, 18 terminate at their forward ends in narrowed clamping members 95, 97, respectively. The motor and lead screw assemblies are secured to the respective arms by yoke members 98 which comprise a pair of shells having a cutaway at their central portion of a size and shape to accommodate the motor and lead screw assemblies with the shells being secured together by a suitable fastener 100.

Each arm 12, 14 terminates at its remote end in an upstanding boss 102, 104 to which is secured the stationary clamping jaws 20, 22.

Mounted between the stationary and the sliding clamping jaws are a pair of tube holders 106, 108 which is in the form of a pair of blocks each of which includes three upstanding vertical walls 110, 112, 114 to form a pair of tube receiving pockets or grooves. Tube holders 106, 108 are spaced apart a distance at least slightly larger than the thickness of wafer 24 to permit the wafer 24 to pass therebetween during the cutting operation. Tube holders 206, 108 are each slidably mounted on its respective arm 14, 16. This slidable mounting is accomplished by mounting each tube holder on a slide strip 116 which is disposed in a groove in each respective arm beneath T-tracks 80. Accordingly, the slide strips are trapped below each respective T-track 80 to prevent the tube holders 106, 108 from being dislodged, but to permit the tube holders to freely slide in a longitudinal direction.

When motors 84 and 86 are operated to drive lead screws 88, 90 in their forward direction, clamping jaws 16, 18 move forwardly into contact with the upper most tube T which is placed in aligned pockets of tube holders 106, 108. The continued forward movement of clamping jaws 16, 18 drives tube holders 106, 108 in the forward direction until the downstream tube T which is placed in the other set of aligned tube holder pockets comes into contact with fixed clamping jaws 20, 22. The continued forward movement of clamping jaws 16, 18 thereby causes both tubes T, T to be pressed toward a flattened condition.

Tube holder 106 includes a hole extending completely through one of its tube holding pockets for access to cam follower 30. In this respect, cam follower 30 is secured to arm 12 by an eccentrically mounted screw 118. The feature of permitting access through the tube holder allows adjustment of the position of cam follower 30 to assure proper contact with cam track 32 formed in the surface of base 40. Thus, by rotation of eccentric screw 118 the position of cam follower 30 may be controlled and thereby achieve the desired contact. When welder 10 is in the condition shown in FIG. 6 ball or roller 28 secured to arm 14 is located in detent 34 of arm 12. Cam follower 30 is in the wide portion of cam track 32. Spring 54 mounted on screw 56 in carriage 46 reacts against arm 12 to pivot arm 12 about pivot rod 36 and thereby effect the butt welding operation.

Any suitable tube heating and cutting means may be used in accordance with this invention. Such tube heating and cutting means may take the forms known in the prior art or may be in the form illustrated and described in copending application Ser. No. 1955 filed Jan. 9, 1987, the details of which are incorporated herein by reference thereto. It is to be understood that within the broad practice of this invention, separate heating and cutting means may be used. In the illustrated embodiment however, a heated wafer is utilized to simultaneously accomplish both actions.

In the illustrated embodiment, the electrical contact for wafer 24 is provided by spring type contact clips 120 pivotally mounted to upright 25 by pivot pin 121. The suitable wiring 122 is also partially illustrated in the drawings.

In accordance with another aspect of this invention, lead screw 64 terminates in a shaft portion 124 which includes a slot 126. An emitter and diode assembly 128 is disposed for sensing the rotation of shaft 124 by counting the number of revolutions of the shaft in accordance with the movement of slot 126. This counting information is sent to a micro-processor (not shown) which includes the general control system for welder 10. The micro-processor would control when, for example, wafer 24 is actuated and would also control the direction of movements of the various motors in accordance with predetermined counts.

Figure 9:
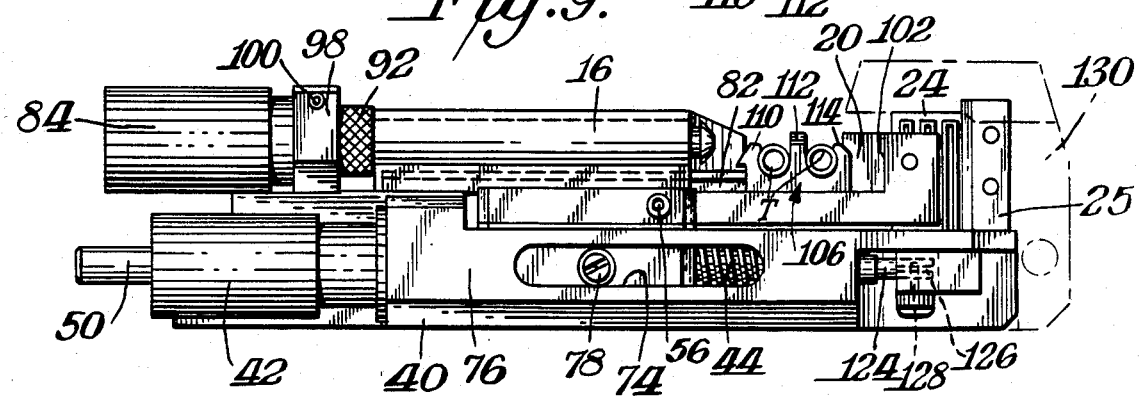
FIG. 9 is a side elevation view of the linear welder shown in FIGS. 1–8 in the phase of operation shown in FIG. 1.
Figure 11:
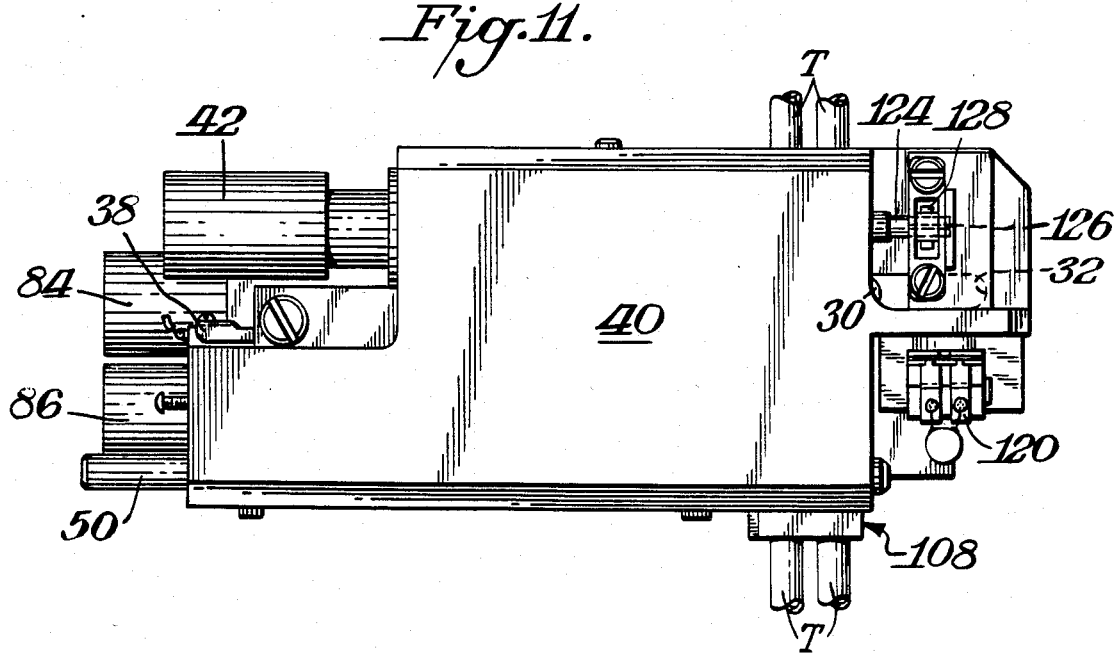
FIG. 11 is a bottom plan view of the linear welder shown in FIGS. 9-10.

Since the operation of welder 10 may result in vapors being created from the heated tubes, FIG. 9 illustrates in phantom the provision of a vapor gas hood 130 which would be connected to a suitable suction source for drawing away such vapors.

The following is a brief summary of the operation of linear welder 10 which is illustrated in FIGS. 1–19.

The linear welder 10 is designed to have two arms 12, 14 which hold the tubes in position for welding. The arms are mounted to a main carriage block 46.

In the reset position, the compression spring 54 tries to force the pivot arm 12 to rotate counter-clockwise into the shift arm 14. But, it can not do this because the roller 28 is resting against the side of the pivot arm 12 and the pivot arm 12 can not rotate.

A cam slot 32 is cut into base 40. The cam follower 30 (on the underside of the pivot arm 12) is in the wide portion of the cam slot 32. When a weld command is received, both arms are driven into the hot wafer 24 by means of the lead screw and motor arrangement. Both arms move as a unit in the minus Y direction until both tubes have been cut by the hot wafer 24. At this point the cam follower 30 is in contact with the walls of the cam track 32 in the narrow portion thereof.

At this point the shift arm 14 hits an obstruction 26 and stops. The carriage 46 and pivot arm 12 continue on until the shift arm 14 and pivot arm 12 are misaligned by the correct amount at which time the main drive motor 42 pauses briefly and then reverses. The roller 28 and pocket 34 on the sides of the pivot and shift arms are now aligned. The function of keeping the arms apart has been taken over by the cam follower 30. The tubes are moved in the plus Y direction until the tubes to be joined are positioned as close to the edge of the wafer 24 as possible without actually leaving the wafer. At this point the carriage 46 stops to allow the stub ends of the tubes to be joined to become molten. This kills any bacteria which may have entered the weld zone and also builds a large melt pool of PVC—which makes the resulting weld far stronger and sealed far better than it would have been if the tubes were simply slid off the wafer.

When the tubes have paused long enough, the drive motor 42 starts again. As the arms move in the plus Y direction the cam follower 30 keeps them apart until the tubes to be welded have just come off of the wafer 24 at which point the cam track 32 allows the pivot arm 12 to be driven into the shift arm 14 by means of the spring force 54.

At this point the unit stops to allow unloading of the welded tube. Since the welding motion begins just as soon as tubes leave the wafer, the forwardmost tube on the pivot arm is still on the wafer, this means that this stub end will be driven into the hot wafer as the weld is taking place—forcing PVC into the "pocket" (slight open area at end of severed tube) which gives stub sealing for "free".

When reset is desired, the carriage 46 will start up and continue in the plus Y direction until the lower end of the shift arm 14 hits another obstruction at which point it stops. The carriage 46 and pivot arm 12 continue until the two arms are realigned. During this process the pivot arm swings clockwise about its pivot as the roller 28 on its side rolls up the side wall of the pocket 34 in the pivot arm.

Since the drive motor 42 may not stop accurately enough to consistently make perfectly aligned welds, a detent arrangement 66, 68, 70 is located on the side of the shift arm.

FIGS. 20–21 deal with an aspect of this invention to assure a sterile welding. As shown in FIG. 21 the tubes T move in the direction indicated by the arrow 132 toward wafer 24. The lines 134 indicate the direction that the tube material, such as PVC, would drag which would be parallel to but opposite the direction of the arrow 132. As shown in FIGS. 20–21 a pair of pockets 136 are stamped or etched into wafer 24 so that less PVC is depleted from the corners of the tube.

FIGS. 22–29 are directed to an aspect of this invention relating to the details of the clamping jaws. As shown in FIG. 22 a clamping jaw 138 is formed in a contour by having notches 140 at the ends thereof so as to form the tube T of a corresponding contour when flattened by a pair of such jaws 138.

Figure 23:
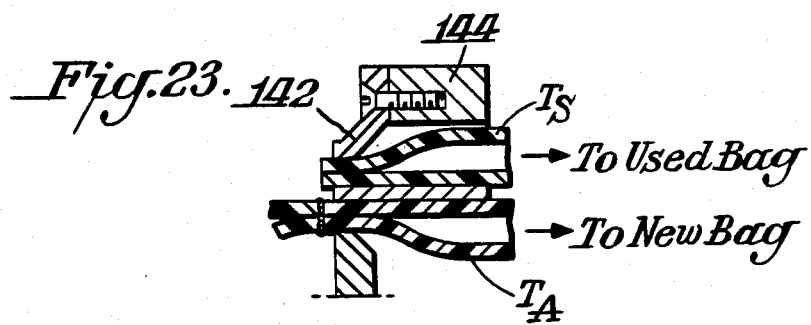
FIGS. 23-29 are cross-sectional plan views showing various clamping jaw modifications in accordance with this invention.

FIG. 23 illustrates a simple tack seal produced by the type of clamping jaw 142 which is mounted in an immobile fashion to support 144. The arrangement would be useful for continuous ambulatory peritoneal dialysis (CAPD). As illustrated, the aligned tubes $T_A$ are shown butt welded together with a tack seal produced on the stub end $T_S$.

Figure 24:
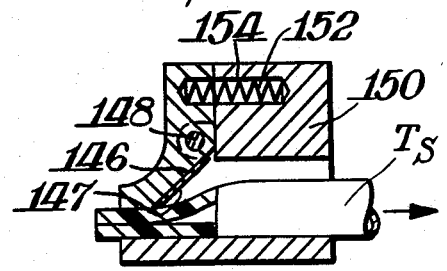
Figure 25:
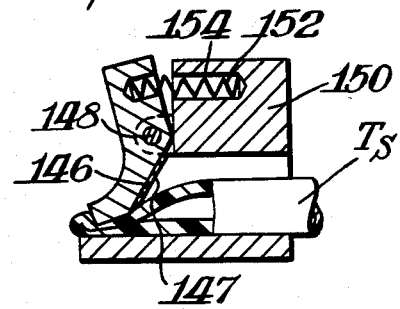

FIGS. 24–29 illustrate an improved manner of forming a seal for the stub end. As illustrated in FIGS. 24–25 the clamping jaw 146 having a foil heater 147 is pivotally secured by pivot pin 148 to support 150 with a compression spring 152 mounted in a pocket 154 formed between the clamping jaw 146 and the support 150. FIG. 24 illustrates the condition of the stub $T_S$ before sealing while FIG. 25 illustrates a more effective seal as the clamping jaw is moved to its final condition and spring 152 rotates the jaw 146 in such a manner as to produce a Hematron type stub seal.

Figure 26:
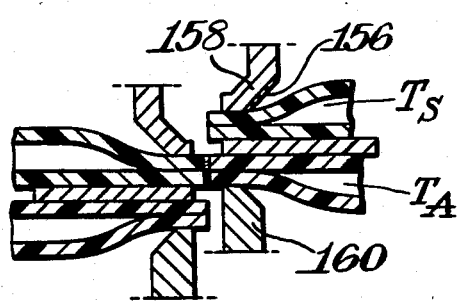
Figure 27:
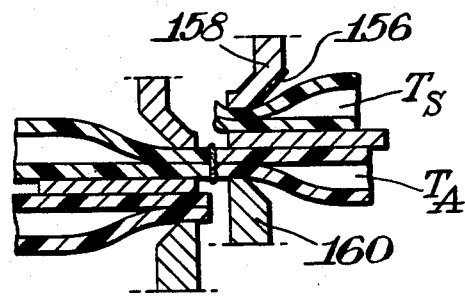
Figure 28:
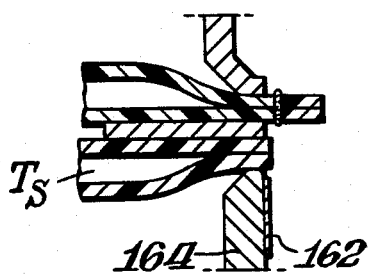

The arrangement of FIGS. 24–25 is not as necessary where the tubes have sufficient natural resiliency. FIGS. 27–28 show a further arrangement for achieving an effective seal without utilizing pivoted clamp jaws. As indicated therein, a foil heater 156 is located between the front jaw 158 and the tube stub $T_S$. Front jaw 158 is fixed and does not pivot. Heater 156 heats up until the plastic next to it begins to soften. As the plastic melts the stub will be compressed against the front jaw by the natural resiliency of the tube in the rear jaw 160. FIG. 26 illustrates the conditions after the welding but before the sealing cycle. FIG. 27 illustrates the conditions after the tubes have been flattened and sealed.

Figure 29:
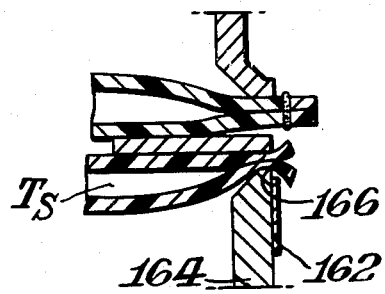

A very similar technique can be used where a total seal of a new bag stub $T_S$ is required. In this case, the foil heater 162 is mounted on the near jaw 164. FIG. 28 illustrates the condition before the seal is effected and FIG. 29 illustrates the resulting seal 166.

Figure 30:
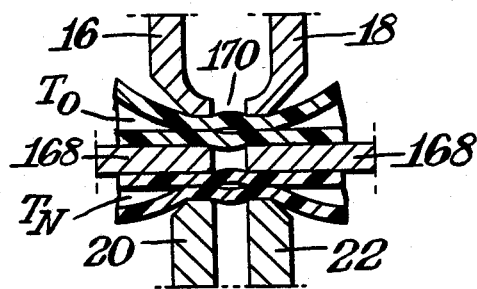
FIGS. 30-33 are cross-sectional plan views illustrating a tube detector for the linear welder of this invention.
Figure 31:
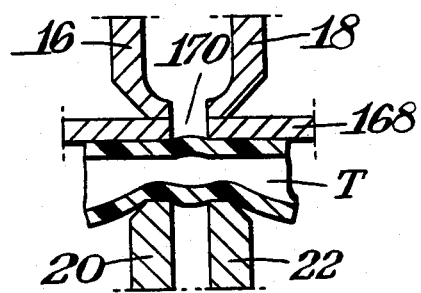
Figure 32:
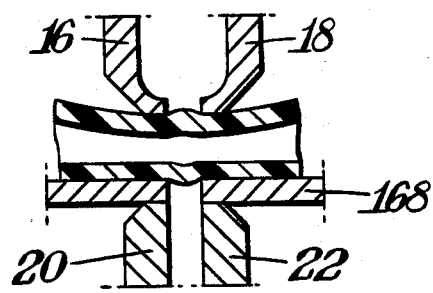
Figure 33:
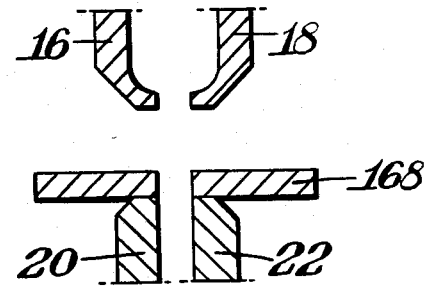

FIGS. 30–33 relate to another aspect of this invention for detecting if a tube is missing from the linear welder. In the illustrated embodiment, the welder 10 is being utilized for securing a tube leading from a patient to a tube having new dialysate by cutting the used dialysate bag tube and realigning the tube leading from the patient to the new dialysate bag. In accordance with the embodiment of FIGS. 30–33 a tube separate bar 168 is disposed between tube $T_O$ which is the tube for the old bag and tube $T_N$ which is the tube for the new bag. The tube holders, may for example, include a single groove or pocket for receiving both tubes and the separator bar 168, might for example, be biased by a spring (not shown) in a direction toward the fixed clamping jaws 20, 22. Separator bar 168 is in the form of two individual bar members with a gap 170 between the bar members to permit the passage of the wafer. Because of the way the tubes are flattened in the welder, the final position of the separate bar 168 will indicate when the operator has forgotten to install one or both tubes. FIGS. 30, for example, illustrates the condition where both tubes are present. FIG. 31, however, illustrates the condition where by old bag is missing. The position of the separator bar 168 is sensed by, for example, a micro-switch which detects that the separator bar 168 is in the correct position for welding. Similarly, FIG. 32 illustrates the condition where the new bag is missing and tube $T_N$ is thus omitted. Finally, FIG. 33 illustrates the condition where both tubes have been omitted. Separator bars 168 would be urged toward clamping jaws 20–22 by means of the return spring. Depending upon the accuracy of the tube separator position detector, the system can also detect differences in tube wall thicknesses between the new and used bags because a difference in thickness would result in the separator bar being off center. This could be used to weld, for example, tubes with differing wall thicknesses.

FIGS. 34–39 relate to an aspect of this invention relating to the sealing of the stub section by means of the surface tension of the plastic tube. FIG. 34 illustrates the condition when the cutting operation has taken place by wafer 24 cutting through tube T. FIG. 35 illustrates the condition after one of the tube sections has been pulled slightly away from wafer 24. Because of the surface tension of the melt pool around the end of the stub the PVC from the tube will be drawn to the weld lines. For example, FIG. 36 illustrates melted PVC 172 to result between wafer 24 and tube T immediately after the cut. The end of tube T is spaced from wafer 24 by the distance $h_1$. FIGS. 37–39 illustrate the radiant heat from the wafer creating a pool, whereby upon further pulling of tube T away from wafer 24 the resultant pool will seal any small holes remaining. It is noted that the thickness of the pool $h_2$ of FIG. 39 is greater than $h_1$, thus giving a much stronger seal.

Figure 42:
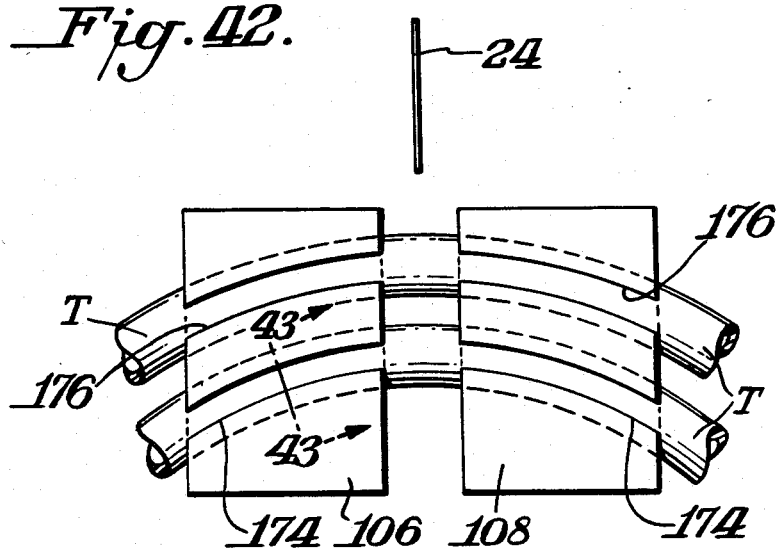

FIGS. 40–44 are related to an aspect of the invention dealing with tube alignment considerations prior to welding. One of the problems for any design for flat tube welders, is that there must be sufficient room for the apparent growth of the tube in one direction as it is flattened at 90° to that direction. This means that there must be some finite unsupported area around the wafer. FIG. 40 illustrates the conditions of this problem, wherein the unsupported area is indicated by the letter A. Tubing is usually stored in a coiled state and tends to coil up and remain coiled when put in the jaws. If one tube had a natural curve upwards and the other a curve downward, a severe mismatch in vertical alignment would result in the final weld. FIGS. 41 and 42 illustrate one manner of overcoming this problem. As indicated therein, the tube holder pockets are formed of arcuate shape so that the tubes are thus placed in a bent condition. FIG. 41, for example, shows a form where the tubes T are bent as mirror images to each other. FIG. 42, however, illustrates the condition where the tube holder pockets 174, 176 in the tube holders 106, 108 are bent parallel to each other.

Figure 43:
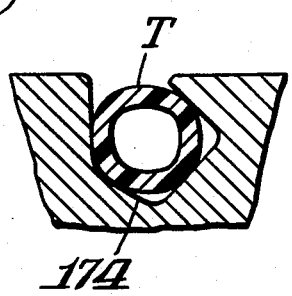
FIG. 43 is a cross-sectional view taken through FIG. 42 along the line 43—43.
Figure 44:
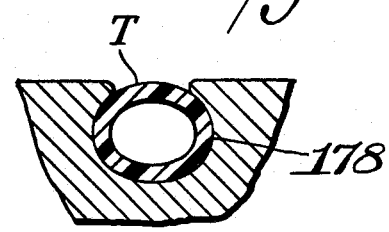
FIG. 44 is a view similar to FIG. 43 of a modified form of this invention.

The tube holder pockets 174 may also be formed in a configuration designed to effectively maintain the tubes held in those pockets. FIG. 43, for example, illustrates a non-uniform pocket 174 which would assist in locking the tube T in place. FIG. 44 illustrates a modified pocket 178 which is of generally eliptical form and extends more than half-way around the tube T to also assist in locking the tube in place.

Figure 46:
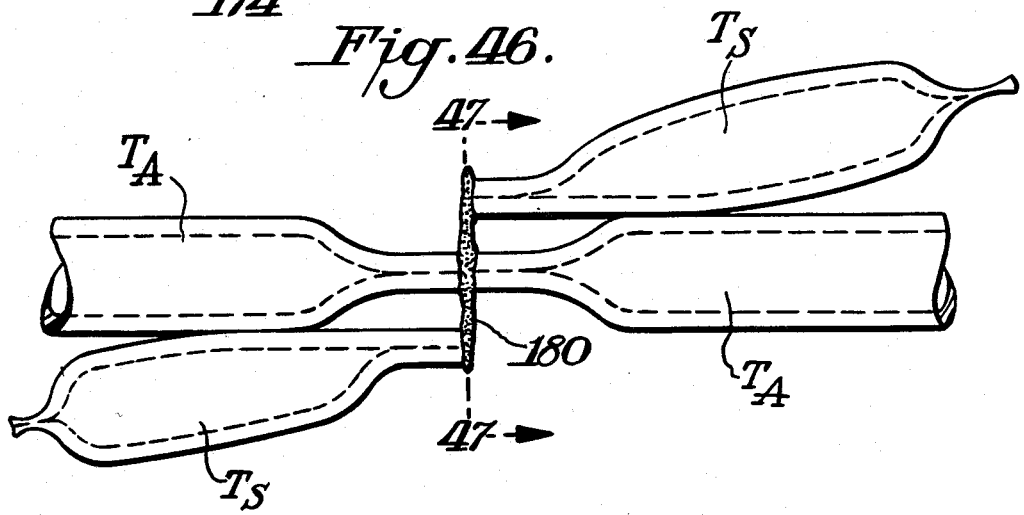
FIG. 46 is a plan view showing the tubes of FIG. 45 after being cut, realigned, and welded.
Figure 47:
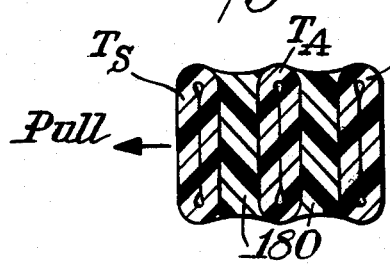
FIG. 47 is a cross-sectional view taken through FIG. 46 along the lines 47—47.
Figure 48:
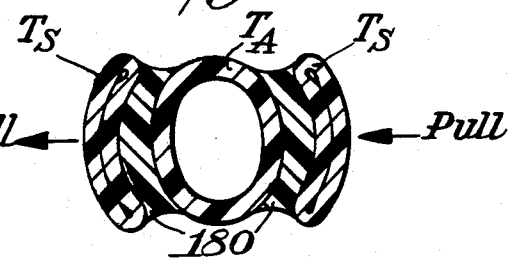
FIG. 48 is a view similar to FIG. 47 showing the realigned tubes in their opened condition.

FIGS. 45–48 are directed to the aspect of this invention relating to reopening the butt welded tube sections. FIG. 45 illustrates the arrangement generally used wherein a pair of tubes $T_1$ and $T_2$ are spaced apart by the distance h and moved toward a wafer 24. FIG. 46 is a top plan view illustrating the tubes after the welding operation wherein a thin web 180 extends from one tube stub $T_S$ past the aligned tubes $T_A$ to the other stub $T_S$. As illustrated in FIG. 47, the flattened tubes have their inner surfaces contacting each other. If stubs $T_S$ and $T_S$ are held and pulled apart, the resultant action is illustrated in FIG. 28 wherein the stress concentration at the top and bottom of the web 180 aids in causing the stubs to break away from the welds and causes the aligned tubes $T_A$ to pop apart and become open. Advantageously, no tools are required to create communication for an opening of the tube sections $T_A$, $T_A$, rather the communication results merely by pulling the stubs apart.

FIGS. 40–50 deal with another variation of this invention relating to the wafer design. FIG. 49 illustrates the common approach wherein the wafer 24 has a straight edge 182. In this arrangement the melt point would take place simultaneously along the edge 182 over the full length of the tube T.

FIG. 50 illustrates a variation of the design of FIG. 49 wherein the wafer 24 includes a slanted edge 184 which is at an angle to the tube T. In FIG. 50 the melt point takes place gradually across tube T. This helps to minimize the size of the welt point so that temperature drops across the flattened tubes are also minimized.

As can be appreciated the present invention thus provides a linear welder which effectively makes a sterile welding of plastic tubes. Various aspects of the invention relating to different modifications may be used in various combinations in accordance with the needs and desires of the user without departing from the spirit of this invention.

What is claimed is:

1. A linear welder for butt welding tubes comprising a stationary base, a carriage slidably mounted on said base, a pair of side by side arms secured to said carriage, a pair of spaced tube holders, each of said tube holders being mounted on a respective arm and having a plurality of tube receiving grooves, said grooves of one holder being selectively in line with said grooves of the other holder whereby a pair of tubes may be placed in said holders across said arms, clamping means on said arms for clamping the tubes in said holders, cutting means, drive means for moving said arms toward said cutting means to dispose said cutting means in the spacing between said holders to cut the tubes into tube sections, said drive means being capable of moving one of said arms forwardly of the other of said arms to realign the tube sections and being capable of moving the realigned tube sections out of contact with said cutting means, means for heating the realigned tube sections, one of said arms being pivotally mounted on said carriage for pressing the realigned heated tube sections into contact with each other for the butt welding, one of said arms being a pivot arm pivotally secured at one end to said carriage, the other of said arms being a shift arm which is mounted for relative sliding movement on said carriage, stop means in the path of motion of said shift arm, and locking means selectively securing said shift arm to said carriage in one of two positions.

2. The welder of claim 1 wherein said cutting means and said heating means comprises a heated wafer.

3. The welder of claim 2 wherein said wafer includes pockets formed in its surfaces thereof.

4. The welder of claim 2 wherein said wafer has an angled lead edge.

5. The welder of claim 1 wherein said clamping means comprises a pair of slidable clamp jaws, one of said clamp jaws being mounted on said pivot arm and the other of said clamp jaws being mounted on said shift arm, a pair of stationary clamp jaws, one of said stationary clamp jaws being mounted on said pivot arm with its tube holder and the other of said stationary clamp jaws being mounted on said shift arm, said tube holders being slidably mounted on said arms, each of said tube holders being between a respective stationary clamp jaw and a slidable clamp jaw, and drive means for moving said sliding clamp jaws on said arms toward and away from said stationary clamp jaws.

6. The welder of claim 5 wherein said pivot arm includes a cam follower, a cam track being provided in said base with said cam follower disposed in contact with said cam track, spring means urging said pivot arm toward said shift arm, one of said arms having a roller and the other of said arms having a detent, said arms being maintained a fixed distance apart when said roller is disposed at a location other than said detent, and said spring means urging said pivot arm toward said shift arm when said roller is in said detent.

7. The welder of claim 6 wherein said cam track includes a narrow neck portion and a widened portion, and said pivot arm being urged into contact with said shift arm when said cam follower is in said widened portion.

8. The welder of claim 7 wherein guide means is provided for guiding said carriage with respect to said base, said guide means including a slot in said base, a guide roller secured to said carriage and positioned in said slot, said carriage having a groove in one of its sides, and a guide rod mounted to said carriage and disposed in said groove.

9. The welder of claim 8 including a motor and lead screw assembly for each of said arms, said lead screw of each assembly being engaged in a threaded bore in each of said arms, a further motor and lead screw assembly mounted on said base, and said carriage having a threaded bore engaged by said lead screw of said further motor and lead screw assembly.

10. The welder of claim 9 wherein said locking means includes a spring arm mounted to said shift arm, said spring arm having a flange, a projection extending from said flange, said carriage having a pair of detents, and said projection being selectively positioned in each of said detents.

11. The welder of claim 10 wherein a rail is mounted in each of said arms, and each of said sliding clamp jaws having a groove which comprises a track for said rails.

12. The welder of claim 11 wherein each of said tube holders is mounted on a slide plate, and each slide plate being positioned at least partially under said rails.

13. The welder of claim 12 wherein said cam follower is an eccentrically mounted roller, and one of said tube holders having an opening therethrough to permit access to said cam follower.

14. The welder of claim 13 wherein said heating means and said cutting means is a heated wafer mounted to said base.

15. The welder of claim 14 wherein said lead screw of said further motor and lead screw assembly terminates in a shaft portion having a slot, and sensor means disposed for counting the number of revolutions of said slot in said shaft portion.

16. The welder of claim 1 wherein said clamping means includes contoured clamping jaws.

17. The welder of claim 1 wherein said tube holder grooves extend more than 180° around the tubes.

18. The welder of claim 1 wherein said tube holder grooves are of irregular cross-section.

19. The welder of claim 1 wherein said pivot arm includes a cam follower, a cam track being provided in said base with said cam follower disposed in contact with said cam track, spring means urging said pivot arm toward said shift arm, one of said arms having a roller and the other of said arms having a detent, said arms being maintained a fixed distance apart when said roller is disposed at a location other than said detent, and said spring means urging said pivot arm toward said shift arm when said roller is in said detent.

20. The welder of claim 1 wherein guide means is provided for guiding said carriage with respect to said base, said guide means including a slot in said base, a guide roller secured to said carriage and positioned in said slot, said carriage having a groove in one of its sides, and a guide rod mounted to said carriage and disposed in said groove.

21. A linear welder for butt welding tubes comprising a stationary base, a carriage slidably mounted on said base, a pair of side by side arms secured to said carriage, a pair of spaced tube holders, each of said tube holders being mounted on a respective arm and having a plurality of tube receiving grooves, said grooves of one holder being selectively in line with said grooves of the other holder whereby a pair of tubes may be placed in said holders across said arms, clamping means on said arms for clamping the tubes in said holders, cutting means, drive means for moving said arms toward said cutting means to dispose said cutting means in the spacing between said holders to cut the tubes into tube sections, said drive means being capable of moving one of said arms forwardly of the other of said arms to realign the tube sections and being capable of moving the realigned tube sections out of contact with said cutting means, means for heating the realigned tube sections, one of said arms being pivotally mounted on said carriage for pressing the realigned heated tube sections into contact with each other for the butt welding, said clamping means including a clamping jaw pivotally connected to a support, resilient means urging said clamping jaw into contact with the tube, and a foil heater secured to said clamping jaw.

22. A linear welder for butt welding tubes comprising a stationary base, a carriage slidably mounted on said base, a pair of side by side arms secured to said carriage, a pair of spaced tube holders, each of said tube holders being mounted on a respective arm and having a plurality of tube receiving grooves, said grooves of one holder being selectively in line with said grooves of the other holder whereby a pair of tubes may be placed in said holders across said arms, clamping means on said arms for clamping the tubes in said holders, cutting means, drive means for moving said arms toward said cutting means to dispose said cutting means in the spacing between said holders to cut the tubes into tube sections, said drive means being capable of moving one of said arms forwardly of the other of said arms to realign the tube sections and being capable of moving the realigned tube sections out of contact with said cutting means, means for heating the realigned tube sections, one of said arms being pivotally mounted on said carriage for pressing the realigned heated tube sections into contact with each other for the butt welding, said clamping means including a clamping jaw, and a foil heater mounted to said clamping jaw.

23. A linear welder for butt welding tubes comprising a stationary base, a carriage slidably mounted on said base, a pair of side by side arms secured to said carriage, a pair of spaced tube holders, each of said tube holders being mounted on a respective arm and having a plurality of tube receiving grooves, said grooves of one holder being selectively in line with said grooves of the other holder whereby a pair of tubes may be placed in said holders across said arms, clamping means on said arms for clamping the tubes in said holders, cutting means, drive means for moving said arms toward said cutting means to dispose said cutting means in the spacing between said holders to cut the tubes into tube sections, said drive means being capable of moving one of said arms forwardly of the other of said arms to realign the tube sections and being capable of moving the realigned tube sections out of contact with said cutting means, means for heating the realigned tube sections, one of said arms being pivotally mounted on said carriage for pressing the realigned heated tube sections into contact with each other for the butt welding, and said tube holders including at least one separator bar for being positioned between the tubes and indicating when a tube is missing.

24. A linear welder for butt welding tubes comprising a stationary base, a carriage slidably mounted on said base, a pair of side by side arms secured to said carriage, a pair of spaced tube holders, each of said tube holders being mounted on a respective arm and having a plurality of tube receiving grooves, said grooves of one holder being selectively in line with said grooves of the other holder whereby a pair of tubes may be placed in said holders across said arms, clamping means on said arms for clamping the tubes in said holders, cutting means, drive means for moving said arms toward said cutting means to dispose said cutting means in the spacing between said holders to cut the tubes into tube sections, said drive means being capable of moving one of said arms forwardly of the other of said arms to realign the tube sections and being capable of moving the realigned tube sections out of contact with said cutting means, means for heating the realigned tube sections, one of said arms being pivotally mounted on said carriage for pressing the realigned heated tube sections into contact with each other for the butt welding, and said tube holder grooves being non-linear.

25. The welder of claim 24 wherein said tube holder grooves are parallel to each other.

26. The welder of claim 24 wherein said tube holder grooves are mirrored images of each other.

27. In a process for the welding of fluid filled plastic tubes wherein the plastic tubes are mounted in a pair of tube holders, flattening the plastic tubes, cutting through the flattened plastic tubes one tube at a time by a heated wafer to form two sets of severed ends, forming molten material at each severed end by means of the heated wafer, realigning the plastic tubes so that one molten severed end of one plastic tube becomes aligned with a molten severed end of the other plastic tube, and butt welding the aligned molten severed ends by pressing the molten severed ends against each other, the improvement being in flattening the plastic tubes in parallel planes perpendicular to the direction of relative motion of the heated wafer, and passing the heated wafer through the planes of the flattened plastic tubes in a direction perpendicular to said planes.

28. The process of claim 27 wherein after the realigned tube ends are welded together the welded tube ends and remaining stub ends are removed from the clamping devices and a lumen is re-established by pulling the un-aligned ends away from the welded tube ends.

29. The process of claim 27 wherein the realigned severed ends are paused while in contact with the wafer to insure that a hot melt pool is available for the subsequent welding step.

30. The process of claim 29 wherein the tubes follow a straight path onto the wafer and retrace that path in coming off the wafer to replenish the hot melt pool.

31. The process of claim 30 wherein the tubes are contour severed in a non-planar manner.

* * * * *